United States Patent [19]

Fraefel et al.

[11] 4,383,832

[45] May 17, 1983

[54] PROCESS FOR THE PREPARATION OF NEW ORGAN TRANSPLANTS

[75] Inventors: Wolfgang Fraefel, Grolley; Heinz F. Lichti, Riehen; Massimo Brunetti, Birsfelden, all of Switzerland

[73] Assignee: Solco Basel AG, Basel, Switzerland

[21] Appl. No.: 394,079

[22] Filed: Jul. 1, 1982

Related U.S. Application Data

[63] Continuation-in-part of Ser. No. 248,782, Mar. 30, 1981, abandoned.

[30] Foreign Application Priority Data

Mar. 31, 1980 [CH] Switzerland .................... 2529/80

[51] Int. Cl.³ .................... A01N 1/00; A61F 1/22
[52] U.S. Cl. .................... 8/94.11; 8/94.33
[58] Field of Search .................... 8/94.11

[56] References Cited

U.S. PATENT DOCUMENTS

| | | | |
|---|---|---|---|
| 3,093,439 | 6/1963 | Bothwell | 8/94.11 |
| 3,166,074 | 1/1965 | Kurilla | 128/335.5 |
| 4,082,507 | 4/1978 | Sawyer | 8/94.11 |
| 4,120,694 | 10/1978 | Schechter | 8/94.11 |

FOREIGN PATENT DOCUMENTS 1063330 10/1956 Fed. Rep. of Germany .
1470805 7/1973 Fed. Rep. of Germany .

*Primary Examiner*—Maria Parrish Tungol
*Attorney, Agent, or Firm*—Ladas & Parry

[57] ABSTRACT

The organ transplants are intended to be used as a replacement (prostheses) for organs or parts of organs, for examples arteries or veins, which have undergone pathological change or are functionally impaired. The organs, which are taken from a fish, bird or higher mammal, are subjected to crosslinking of the amino groups and of the alcoholic hydroxyl groups of the peptide chains of the intercellular matix by means of a di-, tri- or poly-carboxylic acid. It is advantageous subsequently to treat the crosslinked product with a dialdehyde, in order to bind amino groups which have not reacted, or to free the crosslinked product from material which potentially may act as an antigen, by hydrolysis with ficin, papain or a protease having a smaller action. After the hydrolysis, a comprehensive crosslinking is appropriately ensured using a dialdehyde or a di-, tri- or poly-carboxylic acid. The resulting prostheses are distinguished by chemical stability, biophysical and biochemical properties similar to those of the natural material and the absence of rejection reactions.

12 Claims, No Drawings

PROCESS FOR THE PREPARATION OF NEW ORGAN TRANSPLANTS

Continuation-in-part of application Ser. No. 248,782, filed Mar. 30, 1981, now abandoned.

The prosthetic material available in reconstructive surgery for organs or parts of organs which have undergone a pathological change or are functionally impaired covers several possibilities (F. Largiadèr, "Organ Transplantation", 2nd edition, Georg Thieme Verlag, Stuttgart 1970). Specifically, the original organ or part of an organ can be replaced: by endogenous material, for example autologous veins [G. E. Mavor et al., J. Cardiovasc. Surg. 16 (1975), 130], by implants made of plastic [M. E. De Bakey et al., "Fifteen Years' Experience with Dacron Vascular Prostheses", Brochure, Baylor Coll. Med. 1971 (Amer. Coll. Surg. Exhibit. 1971)] or by appropriately prepared transplants from diverse species of animals (P. Walter and H. Schmitz, "Der heterologe Gefässersatz" ("Heterologous Vascular Replacement"), Editio Cantor, Aulendorf 1976).

The latter originate in the main from animal organs or parts thereof (for example the carotid arteries of calves or cardiac valves from pigs), which after removal are freed, by means of an enzymatic hydrolysis (for example with ficin), from proteins which potentially act as antigens. The intercellular matrix remaining after this treatment consists in the main of collagenous fibres of type I. In order to impart to this collagen skeleton obtained after proteolytic hydrolysis the density and stability necessary for a prosthesis, a so-called "tanning" is carried out. Aldehydes, such as dialdehyde starch, glutaraldehyde and paraformaldehyde, as well as glyoxal and polyacrolein and also acetaldehyde and crotonaldehyde, are available for this tanning—or crosslinking. The common characteristic of these substances used for crosslinking is that they react with the $\epsilon$-amino groups of the lysine residues in the collagen peptide chain with the formation of Schiff's bases.

However, with organs pre-treated in this way, such as, for example, vascular prostheses (U.S. Pat. No. 3,093,439, U.S. Pat. No. 4,120,649 or Swiss Pat. No. 595,105) it has been found that the biophysical characteristics originally present, such as the elasticity in the axial and radial directions and also the extremely smooth nature of the inner surface of the vessels, are completely lost as a result of the enzymatic degradation by means of ficin. As a consequence of this, it has to date not been possible to meet the demands for an ideal vascular prosthesis of biological material. The same also applies in the case of the replacement of other organs or parts of organs. If, on the other hand, the ficin degradation is omitted, the danger of an antigen effect cannot be excluded, such as, for example, in the process for the preparation of natural tissue for implantation in accordance with German Offenlegungsschrift 2,519,107.

A further modification of the collagen skeleton comprises binding aliphatic carboxylic acids covalently to the side chain of aminoacids by acylation, with the formation of more highly negatively charged derivatives (as is known an excess positive charge promotes thrombosis) (P. N. Sawyer et. al., "Vascular Grafts", Appleton Century Crofts, New York 1977, page 282 et seq.). Quite generally, the surface charge of the intimal surface of a prosthesis can be rendered more negative or more positive, i.e. less thrombogenic or more thrombogenic, by blocking the positive charges of arginine, lysine, hydroxylysine and histidine, respectively by neutralizing the aspartic and glutamic acid, through reaction with albumin, succinic anhydride, glyoxals, formic acid, ethoxyformic anhydride and 1-ethyl-3-(3-dimethylaminopropyl) carbodiimide (U.S. Pat. No. 4,082,507). However, these procedures do not result in crosslinking between different amino acids of the collagen skeleton.

Despite the efforts described above, clinical experience teaches that the transplants already proposed can, in general, not be regarded as completely satisfactory, at least in the long term (H. Haimovici, "Vascular Surgery, Principles and Techniques", McGraw-Hill, New York 1976, page 304).

It has now been found, surprisingly, that by means of novel intermolecular and/or intramolecular crosslinking of the macromolecules of the intercellular matrix of organs or parts of organs, prior to or even without the proteolytic degradation by means of ficin, the biophysical characteristics originally present, such as, for example, in the case of vascular prostheses, the axial and radial elasticity and the smooth nature of the inner surface of the vessels, are substantially retained.

This crosslinking differs from the known procedures in that it is effected not by the formation of Schiff's bases but by chemically considerably more stable acid amide bonds between the amino groups, or by ester bonds between the alcoholic hydroxyl groups, of the peptide chains of the intercellular matrix and the carboxyl groups of a di-, tri- or poly-carboxylic acid, which is employed as an agent for crosslinking.

The process according to the invention comprises subjecting organs or parts of organs of fishes, birds or mammals, preferably from higher mammals, to crosslinking of the macromolecules of the intercellular matrix by the formation of amide bonds, or ester bonds, between the amino groups, or the alcoholic hydroxyl groups, of the peptide chains and the carboxyl groups of di-, tri- or poly-carboxylic acids of the aliphatic, cycloaliphatic, aromatic or heterocyclic series.

Although it is not essential, a further treatment, in accordance with the following guidelines, of the resulting intercellular matrix crosslinked by amide bonds can bring certain advantages.

Initially, the matrix can be treated in a first additional process stage with formaldehyde or a dialdehyde. This treatment serves in the main to bind any amino groups which have not been bound during crosslinking. As a result of this, the excess negative charge is increased, which, as experience has shown, lowers the danger of thrombosis, for example of vascular transplants (P. N. Sawyer et al., ibidem).

In place of the abovementioned treatment with said aldehyde, the matrix can, in another (alternative) additional process stage, be freed from material which potentially acts as an antigen, by hydrolytic degradation with ficin, papain or another protease of the same or similar substrate specificity. By means of the additional hydrolysis or proteolysis, organ transplants are obtained with which the possibility of an antigen effect, that is to say the triggering of an immunological defence reaction with rejection of the transplant or implant, is excluded, even in the long term.

If the said proteolysis with ficin, papain or the like is carried out, individual amino groups are liberated in the intercellular matrix. In order to bind these groups and the amino groups which may not have been reacted during the preceding crosslinking, it is advisable, in a second additional process stage, either to treat the matrix with formaldehyde or a dialdehyde—as has already been described above—or to subject the matrix to crosslinking again, by forming amide bonds with the aid of one of the di-, tri- and poly-carboxylic acids mentioned.

The invention is described in detail in the text which follows.

The starting material used is in particular arteries, veins, cardiac valves and also the pericardium and the like from birds and higher mammals of a suitable size. Suitable donors are both man himself (autologous transplants) and also calves, cattle, horses, sheep, pigs, geese, turkeys, pheasants and other animals (heterologous transplants). Organs and parts of organs preferred for this purpose are those from animals, because of their more general availability, but in particular those from young animals, because of their excellent elasticity.

It is self-evident that the organs and parts of organs are freed from the surrounding tissue immediately after they have been removed and that, in the case of arteries or veins, the collaterals are tied off by ligature. The organs or parts of organs are then subjected to the process immediately or are stored in water, physiological saline solution or another physiological aqueous solution, for example Tween 80 ® (polyoxyethylene derivatives of the sorbitan oleates), or in a non-aqueous liquid, for example dimethylsulphoxide, optionally with the addition of a little sodium azide, at 0° to −15° C. until the process is employed.

The one stage which always forms part of the process according to the invention comprises crosslinking of the peptide chains of constituents of the intercellular matrix; it is based on the binding of two, three or more amino groups (in the main ε-amino groups of the lysine radicals) or alcoholic hydroxyl groups of the peptide chains by means of aliphatic, cycloaliphatic, aromatic or heterocyclic di-, tri- or poly-carboxylic acids, in the form of acid amide bonds or ester bonds.

Amongst the carboxylic acids mentioned, suitable acids are in particular those which contain neither oxo groups (aldehyde and keto groups) nor amino groups. Di-, tri- and poly-carboxylic acids which can be used are in particular those which do not carry any functional groups except for the carboxyl groups and in some cases hydroxyl groups.

Preferred aliphatic dicarboxylic acids and tri-carboxylic acids are those having not more than 12 carbon atoms, that is to say in particular oxalic acid, malonic acid, succinic acid, malic acid, glutaric acid, adipic acid, pimelic acid, suberic acid, sebacic acid and dodecanedioic acid, and also tartaric acid and mucic acid, and preferred tricarboxylic acids are tricarballylic acid and citric acid.

Amongst the cycloaliphatic di-, tri- and poly-carboxylic acids, suitable acids are, inter alia, the cyclopentanedicarboxylic acids and the cyclohexanedicarboxylic acids, for example cyclohexane-1,4-dicarboxylic acid.

Aromatic dicarboxylic acids which may be mentioned here in particular are phthalic acid, isophthalic acid and terephthalic acid, and aromatic tricarboxylic acids which may be mentioned are trimesic acid and trimellitic acid.

Suitable heterocyclic di-, tri- and poly-carboxylic acids are, inter alia, furan-2,5-dicarboxylic acid, tetrahydrofuran-2,5-dicarboxylic acid, oxidised starch and carboxymethylcellulose.

The existing space between two ε-amino groups accessible for crosslinking and the solubility, in the solvents, appropriate for carrying out the process, make a relatively narrow lower and upper limit appear advisable in the case of the preferred groups mentioned. Thus, particularly preferred acids are, on the one hand, aliphatic dicarboxylic acids having 3 to 12 carbon atoms, i.e. acids ranging from malonic acid to dodecanedioic acid. On the other hand, however, higher molecular polycarboxylic acids, such as, for example, oxidised starch, have also proved particularly suitable.

Crosslinking can be effected on the basis of all of the methods customary in chemistry for forming an amide bond between an amino group and a carboxyl group; in this context see, inter alia, H. D. Law, "The Organic Chemistry of Peptides" (John Wiley & Sons Ltd., London-New York 1970). In particular—without any claim to completeness—the acid chlorides, acid azides or acid anhydrides of the carboxylic acids mentioned can be reacted with the free amino groups of the intercellular matrix. The free di-, tri- and poly-carboxylic acids can also be bonded to the free amino groups of the intercellular matrix with the aid of a suitable coupling reagent, such as the carbodiimides, for example dicyclohexylcarbodiimide.

As a rule, the reaction is carried out in an anhydrous organic solvent, such as tetrahydrofuran, dioxane, pyridine, dimethylformamide, dimethylacetamide, dimethylsulphoxide and hexamethylphosphoric acid triamide, or in a mixture of two or more of these solvents. If a water-soluble coupling reagent, for example N-ethyl-N'-(3-dimethylaminopropyl)-carbodiimide hydrochloride, is employed, water is also suitable as the solvent.

The organs and parts of organs stabilised in this way can now be subjected, in an (optional) second stage of the process, to tanning or crosslinking by means of formaldehyde or a dialdehyde, the amino groups in the collagen-peptide chain which are possibly still free being reacted, with the formation of Schiff's bases. This treatment is also advantageous inasmuch as, in particular, the prostheses obtained with glutaraldehyde are already virtually sterile.

In principle, every dialdehyde is suitable as the dialdehyde. Formaldehyde, dialdehyde starch and in particular glutaraldehyde are preferred. The reaction with the aldehyde is advantageously carried out in aqueous solution, for example in accordance with the method of Swiss Pat. No. 595,105 or U.S. Pat. No. 3,093,439.

Alternatively, the organs or parts of organs stabilised by crosslinking can, if desired, be subjected to the proteolytic effect of a suitable enzyme, without suffering substantial losses in their original biophysical and biochemical properties. This behaviour is to be ascribed to the fact that the peptide chains of the collagen are fixed by the crosslinking, before the stabilising elements of the intercellular matrix, such as elastin, proteoglycans and also structural glycoproteins, are partially removed by the hydrolysis.

The preferred second stage of the process thus comprises an incubation of the organ material in a solution, appropriately an aqueous solution, of ficin, papain or another protease of the same or similar substrate specificity. The hydrolysis or proteolysis is preferably effected with ficin, advantageously in the pH range from 4.0 to 5.5; it can, inter alia, be carried out in accordance with Example 3 of Swiss Pat. No. 595,105.

The repeat crosslinking which advantageously follows the hydrolysis can be carried out with formaldehyde or a dialdehyde or one of the abovementioned di-, tri- and poly-carboxylic acids; the methods described above are suitable for this purpose.

The resulting organ transplants are then washed thoroughly with water, sterilised and stored in heat-sealed plastic bags until they are used. Sterilisation of the products is effected exclusively by chemical means, with the aid of propene-1,2-oxide (see under K-I solution in the experimental section), propiolactone (β-hydroxy-propionic acid lactone) or ethylene oxide.

To summarise, by means of the process according to the invention prostheses are obtained which are particularly suitable as replacements for defective organs or parts thereof, because their intermolecular and intramolecular transverse bonds (acid amide bonds and ester bonds respectively) are distinguished by particular chemical stability, their biophysical properties (elasticity and rigidity) and also their biochemical properties (reduced thrombogenicity) are extremely similar to those of the natural material, as a result of the type of crosslinking mentioned, prior to or even without proteolytic degradation, and they nevertheless cause no rejection reactions, that is to say cannot have an antigen effect.

The advantages of the characteristic features mentioned for surgical use and for the therapeutic results are obvious, and they have in fact already been confirmed in animal experiments.

Mongrel dogs with a body weight of 20 to 25 kg, and the artery transplants prepared according to Example 9, were used for the studies. The prostheses were implanted (a) at the two femoral arteries of each dog, immediately distal of the inguinal ligament, by the method of P. Walter et al. [Helv. chir. Acta 46 (1979), 81 et seq.], (b) at the two carotid arteries, (c) at the abdominal aorta, in the caudal direction from the exits from the renal arteries [P. Walter and H. Schmitz, Der heterologe Gefässersatz (Heterologous Vascular Replacement), page 30, Editio Cantor, Aulendorf 1976], (d) at the infrarenal inferior vena cava by the method of S. Horsch et al. [Langenbecks Arch. Chir. 344 (1978), 225 et seq.]. For comparison, parallel experiments were carried out with prostheses made of Teflon (®) and prostheses made of Dacron (®) and also with umbilical veins which had only been tanned with glutaraldehyde. The occlusion rate of the implants after six weeks was measured.

It should be emphasised here that, in particular, implantation point a (see above) on the hip joint of the dog is subjected to high mechanical stress (flexion), which from time to time increases to a permanent stress. In other words, this test arrangement corresponds to extremely unfavourable physiological conditions.

The results were then also the more informative. The implants of Teflon (®) and the umbilical vein gave an occlusion rate of 100% and the implants of Dacron (®) gave an occlusion rate of 77%, whilst the implants according to Example 9 showed an occlusion rate of 50%. The values obtained from the comparison studies are statistically significant.

In studies under physiologically more favourable conditions, specifically at the Arteria carotis, carried out in the medium term, i.e. over a period of 6 months, the occlusion rate of the implants according to Example 9 fell to 20%; the value determined is statistically significant. In studies in the infrarenal region no thrombosis was observed in the medium term (6 months).

Comparison trials on humans are now in progress in a university hospital.

EXAMPLE 1

Carotid arteries from calves are freed from surrounding connective tissue and the collaterals are tied off. After mechanical preparation, they are washed with deionised water, dried off with absorbent paper, drawn up on a glass rod with a diameter of, for example, 3 mm and placed in a measuring cylinder filled with tetrahydrofuran, for dehydration. The contents of the measuring cylinder are shaken round at 1 to 2 hour intervals. After 5 hours the liquid is replaced by fresh tetrahydrofuran. After a further 2 to 3 hours the glass rods are removed.

The following day the arteries are placed in a 2% (weight/volume) solution of adipic acid chloride in tetrahydrofuran and left in this solution for 24 hours. The solution is occasionally shaken round or circulated by means of a pump. The arteries are then placed in pure tetrahydrofuran, then in tetrahydrofuran/water (1:1 volume/volume) and finally in phosphate-buffered saline solution and are left in each solution for 30 to 60 minutes. The arteries are now ready for sterilisation or for hydrolysis with ficin, papain or the like.

(a) Sterilisation with propene-1,2-oxide

The arteries are placed in a 1% (weight/volume) solution of propene-1,2-oxide in ethanol/water (1:1) (volume/volume) for 16 to 24 hours and possibly even longer. They are then placed under sterile conditions in sterile PBS solution and together with this solution are sealed into sterile plastic bags by heat-sealing.

PBS solution 320 g of sodium chloride, 8 g of potassium chloride, 51.2 g disodium hydrogen phosphate dihydrate, 8.0 g of potassium dihydrogen phosphate, 5.2 g of calcium chloride dihydrate and 4.0 g of magnesium chloride hexahydrate are dissolved in 40 liters of water.

If it is desired to store the arteries in an ethanol/water mixture, it suffices to place them in the abovementioned alcoholic-aqueous propene oxide solution and to seal them, together with the liquid, in plastic bags by heat-sealing.

(b) Sterilisation with propiolactone (β-hydroxy-propionic acid lactone)

The following salts are dissolved in about 900 ml of deionized water: 0.236 g of sodium chloride, 0.248 g of potassium chloride, 0.363 g of calcium chloride dihydrate, 0.190 g magnesium chloride hexahydrate and 0.172 g of potassium dihydrogen phosphate. The pH value of the solution is raised to 7.4 with a little 0.1 N aqueous sodium hydroxide solution. 11.782 g of sodium bicarbonate are then dissolved in the solution and the volume is made up to 1,000 ml by adding water. Immediately before sterilising the arteries, 8.86 ml (10.08 g) of propiolactone are added to 1 liter of this solution, the arteries are placed in the mixture and are sealed together with the liquid in a plastic bag by heat-sealing.

(c) Sterilisation with ethylene oxide

The arteries placed in PBS solution or physiological saline solution are sealed together with the liquid in a plastic bag by heat-sealing. Sterilisation is effected by exposing the sealed plastic bags to ethylene oxide gas for 4 hours at 25° to 30° C. in a sterilisation apparatus, in accordance with a known method.

EXAMPLE 2

Four mechanically prepared calf arteries are individually drawn up onto 4 mm thick glass rods and placed in a 500 ml measuring cylinder filled with pyridine. One hour later the arteries are so still that the glass rods can be removed. The liquid is decanted and replaced by fresh pyridine. After one hour the pyridine is renewed again. After a further one hour, the arteries are placed in a mixture which has been prepared in the following way: 2 ml (2.5 g) of adipic acid chloride are injected into a mixture of 90 ml of pyridine and 2 ml of dimethylformamide, with stirring; a fine precipitate of adipylpyridinium chloride forms. When it has settled, it is covered with a cribriform plate made of porcelain. The arteries are then placed on the cribriform plate, so that they are entirely covered by the liquid but do not come into contact with the precipitate. 18 Hours later the arteries are removed from the liquid and immersed in K-I solution (see Example 9 below) for 30 minutes. They are then washed four times with 0.05 N sterile aqueous acetic acid and twice with sterile phosphate buffer (1/15 molar) of pH 8. Finally, they are placed in sterile PBS solution and sealed together with this liquid into a plastic bag by heat-sealing.

EXAMPLE 3

10 Calf arteries are prepared mechanically and placed vertically for three hours in a 500 ml measuring cylinder filled with tetrahydrofuran. They are then placed individually in glass tubes about 2 cm wide and are each covered with a layer of 40 ml of a 0.06% (weight/volume) solution of adipic acid in tetrehydrofuran/water (4:1) (volume/volume). After one hour 40 ml of a 2% (weight/volume) solution of dicyclohexylcarbodiimide in tetrahydrofuran are added to each tube and mixed with the solution already present by shaking and swinging round. After 3 hours the arteries are placed in K-I solution (see Example 9 below). The following day they are each washed with 40 ml of sterile ethanol/water (1:1) (volume/volume) and with 40 ml of sterile phosphate buffer (1/15 molar) of pH 8 and are placed in sterile PBS solution. Finally, they are sealed together with the PBS solution in plastic bags by heat-sealing.

EXAMPLE 4

After mechanical preparation, 10 calf arteries are placed in a 500 ml measuring cylinder filled with dimethylformamide. After 3 hours the arteries are placed individually in glass tubes with an internal diameter of about 2 cm and 40 ml of a 0.06% (weight/volume) solution of adipic acid in dimethylformamide/water (4:1) are poured over each artery. After one hour, 40 ml of a 2% (volume/volume) solution of dicyclohexylcarbodiimide in dimethylformamide are added to each tube and mixed with the adipic acid solution poured in earlier, by shaking and swinging round. 3 hours later the liquid is poured off from each tube and replaced by 80 ml of K-I solution in each case. The following day the arteries are each washed with 40 ml of sterile ethanol/water (1:1) (volume/volume) and with 40 ml of sterile phosphate buffer (1/15 molar) of pH 8. Finally, they are placed in sterile PBS solution and sealed together with this solution in a plastic bag by heat-sealing.

EXAMPLE 5

4 Calf arteries are freed from connective tissue in the usual way and the collaterals are tied off. They are then placed in 60 ml of 0.02% (weight/volume) aqueous adipic acid solution for 2 hours. They are then placed in 60 ml of an aqueous solution which contains adipic acid in a concentration of 0.2 g per liter and N-ethyl-N'-(3-dimethylaminopropyl)-carbodilmide hydrochloride in a concentration of 25 g per liter. After 20 hours, the arteries are placed in K-I solution and 24 hours later they are placed in sterile PBS solution. They are sealed together with the latter solution in sterile plastic bags by heat-sealing.

EXAMPLE 6

Mechanically prepared arteries are placed in 60 ml of a solution of 0.1% (weight/volume) suberic acid in water for 2 hours and are then placed in 60 ml of an aqueous solution which contains, per liter, 0.24 g of suberic acid and 25 g of N-ethyl-N'-(3-dimethylaminopropyl)-carbodiimide hydrochloride. After 20 hours the arteries are placed in K-I solution and after a further 24 hours they are placed in sterile PBS solution and sealed together with this solution in sterile plastic bags by heat-sealing.

EXAMPLE 7

Calf carotid arteries are treated with adipic acid chloride in tetrahydrofuran using the procedure described in Example 1. The resulting arteries are then not sterilised but are hydrolysed with ficin in the following way:

1 liter of water is warmed to 37° C. 10 g of ficin are added, with stirring; in some circumstances the ficin only partly dissolved. 1 g of cysteine is then added, and dissolved, with stirring. The pH value of the solution is raised to 6.0 with 1 N aqueous trisodium citrate solution. If the liquid is turbid, it is filtered through cotton fabric and freed from the turbidity in this way. Its temperature meanwhile falls to about 25° to 30° C.

The arteries are placed in a measuring cylinder and the clear ficin solution is poured over them. The measuring cylinder is placed in a waterbath at 37° to 38° C., so that its contents warm to about 37° C. The reaction has ended at the latest after 3 hours at 37° C. The ficin solution is new poured off and discarded. The arteries are washed for a quarter of an hour with running deionised water of about 20° C. The water is then poured off. The arteries are still in the measuring cylinder. 1 liter of an aqueous solution which contains 11.9 g of sodium chlorite ($NaClO_2$) is poured over them. After 18 hours at room temperature, the liquid is decanted off and the arteries are washed for about a quarter of an hour with running deionised water at about 20° C. The arteries are now ready for sterilisation or for after-treatment with a suitable aldehyde.

EXAMPLE 8

Calf carotid arteries are treated with adipic acid chloride in tetrahydrofuran using the procedure described in Example 1. The resulting arteries are then not sterilised but are hydrolysed with ficin in the following way:

1 liter of citric acid/phosphate buffer solution of pH 4.5, prepared by the method of T. C. McIlvaine [J. Biol. Chem. 49, 183 (1921)], is initially introduced. 10 g of ficin are added, and dissolved, with stirring. 1 g of cysteine is then added, and dissolved, with stirring.

The arteries are placed in a measuring cylinder and the ficin solution described above is poured over them. The subsequent treatment is in accordance with the method of Example 7.

EXAMPLE 9

As described in Example 7, calf carotid arteries are first crosslinked with adipic acid chloride in tetrahydrofuran and then subjected to hydrolysis with ficin.

Subsequently they are again drawn up on glass rods and placed in a 4% aqueous glutaraldehyde solution. After 24 hours the rods are removed and the arteries are washed for at least 90 minutes in running water. Finally, they are placed in K-I solution and sealed in a plastic bag by heat-sealing.

K-I solution 720 ml of water and 720 ml of ethanol are mixed. 16.9 ml (14.1 g) of propene-1,2-oxide are added to this solution. This solution is always freshly prepared and used for sterilisation immediately after it has been prepared.

EXAMPLE 10

7 Calf pericardia are freed from fat, scraped substantially smooth and placed in 500 ml of tetrahydrofuran in a shallow dish. The liquid is replaced by fresh tetrahydrofuran after 1 day and after 2 days. After a total of 4 days, the pericardia are placed in 500 ml of a 2% (weight/volume) solution of adipic acid chloride in tetrahydrofuran and left in this solution for 1 day. The liquid is then poured off. The pericardia are placed for half an hour in ethanol/water (1:1, volume/volume), this operation being carried out three times, and are then washed for half an hour in running water. They are then placed in a phosphate-buffered saline solution of pH 4.5. They are now ready for hydrolysis with ficin, papain or another suitable enzyme.

The pericardia crosslinked with adipic acid chloride are immersed in a ficin solution as described in Example 7 or 8. The temperature is 37° C. After 3 hours the ficin solution is poured off and the pericardia are washed with running deionised water for a quarter of an hour. They are then placed in an aqueous solution which contains 11.9 g of sodium chlorite per liter. 18 hours later the solution is poured off. The pericardia are washed with running deionized water for a quarter of an hour. They are now ready for after-treatment with a suitable aldehyde or for sterilisation.

The pericardia which have been crosslinked with adipic acid chloride and hydrolysed with ficin are placed in a 1% (weight/volume) aqueous solution of glutaraldehyde for 24 hours, freed from excess aldehyde by washing for two hours in running water and sterilized either with K-I solution or with ethylene oxide.

(a) Sterilisation with K-I solution

The abovementioned pericardia, which finally have been treated with glutaraldehyde and washed, are placed in K-I solution and sealed together with this solution in a plastic bag by heat-sealing.

(b) Sterilisation with ethylene oxide

Each of the abovementioned pericardia, which finally have been treated with glutaraldehyde and washed, is sealed together with 0.9% saline solution in a plastic bag, by heat-sealing. The sealed bags are exposed to ethylene oxide gas for 4 hours at 25° to 30° C. in a sterilisation apparatus.

EXAMPLE 11

Calf carotid arteries are prepared mechanically, as described in Example 1, and washed with water. They are then placed in 200 ml of tetrahydrofuran and this liquid is replaced by fresh tetrahydrofuran after 1, 2 and 4 days. After a total of 7 days, the arteries are placed in a 3.2% (weight/volume) solution of dodecanedioic acid dichloride in tetrahydrofuran and are left in this solution for 48 hours. They are then placed in tetrahydrofuran for 16 hours, in tetrahydrofuran/buffer solution (1:1 volume/volume) of pH 4.5 for 8 hours and finally in aqueous buffer solution of pH 4.5 for one day. They are now ready for sterilisation or for hydrolysis with ficin.

EXAMPLE 12

As described in Example 7 or 8, calf carotid arteries are first crosslinked with adipic acid chloride in tetrahydrofuran and then subjected to hydrolysis with ficin. After washing out the sodium chlorite solution as in Example 7, the arteries are placed in 0.5% aqueous glutaraldehyde solution. After 48 hours the liquid is poured off. The arteries are then washed for half an hour with running water. Finally, they are placed in 0.9% sodium chloride solution and introduced together with this liquid into plastic bags and the bags are heat-sealed. The sealed plastic bags are sterilised by exposing to ethylene oxide gas, as described in Example 1 under section (c).

EXAMPLE 13

550 g of maize starch are introduced into 3 liters of water and stirred for a quarter of an hour. A solution of 705 g of sodium metaperiodate in 9 liters of water is then added dropwise in the course of 1 hour. The suspension is stirred for a further 18 hours. It is then filtered through filter-paper. The residue on the filter is suspended in 1.5 liters of water and the suspension is filtered again. This process of suspending and filtering is repeated five times. The residue on the filter, which is still moist, is then introduced into 3 liters of acetone and the mixture is stirred vigorously for half an hour and then filtered. The filter residue is dried for 42 hours at 40° C. in vacuo. Afterwards, it is round to a fine powder in a ball mill. 13 g of the fine powder are suspended in 1 liter of deionised water. The pH value is adjusted to 8.80 by adding saturated sodium bicarbonate solution.

Arteries, which—as described in Example 7 or 8—have been crosslinked with adipic acid chloride and hydrolysed with ficin, are then placed in the suspension of aldehyde starch obtained above. The liquid is kept in continuous motion with the aid of a vibrator. After 24 hours the liquid is poured off. the arteries are washed in running water for 30 minutes. They are then placed in PBS solution, sealed together with this liquid in a plastic bag by heat-sealing and sterilised by exposing to ethylene oxide gas.

EXAMPLE 14

550 g of maize starch are added to 3 liters of water and the mixture is stirred for a quarter of an hour. A solution of 705 g of sodium metaperiodate in 9 liters of water is then added dropwise in the course of 1 hour. The suspension is stirred for a further 18 hours. It is then filtered through filter-paper. The residue on the filter is suspended in 1.5 liters of water and the suspension is filtered. The process of suspending and filtering off is repeated five times.

Afterwards, the residue is suspended in 3 liters of water. A solution of 695 g of potassium permanganate in 12 liters of water is added dropwise in the course of 1 hour, with continuous stirring. The suspension is stirred for a further 18 hours. The mixture is then allowed to stand for 2 hours. During this time a large proportion of the manganese dioxide formed settles out. The supernatant suspension is transferred carefully, with the aid of a siphon, into another vessel; the sediment is discarded.

The suspension is filtered through filter-paper. The residue on the filter is suspended in 1.2 liters of water and the suspension is filtered. The process of suspending and filtering off is repeated three times. The filter residue is then taken up in 9 liters of 0.5 N hydrochloric acid at 0° C. and stirred for 1 hour. The suspension is then filtered through filter-paper. The residue on the filter is suspended in 1.2 liters of water and the suspension is filtered. The process of suspending and filtering off is repeated three times. The filter residue is then suspended in 3 liters of acetone and the suspension is stirred for half an hour and filtered. The filter residue is dried for 42 hours at 40° C. in vacuo and is then ground to a fine powder in a ball mill.

2 g of this powder, which consists of oxidised starch containing a large number of carboxyl groups, are suspended in 1 liter of water. Mechanically prepared arteries are placed in 150 ml of this suspension for 2 hours. The liquid is agitated gently with the aid of a vibrator. The arteries are then placed in 200 ml of a suspension which contains, per liter, 0.26 g of the abovementioned powder and also 25 g of N-ethyl-N'-(3-dimethylaminopropyl)-carbodiimide hydrochloride. The suspension is subjected to continuous gentle vibration. After 24 hours the liquid is poured off. The arteries are washed for half an hour under running water. They are then placed in 150 ml of citric acid/phosphate buffer solution of pH 4.5 and subjected to the ficin treatment described in Example 8.

EXAMPLE 15

Following mechanical preparation 10 calf arteries are placed in a shallow dish and covered with 500 ml of a 1% solution of citric acid in water(weight/volume). After two hours the arteries are placed in a 500 ml measuring cylinder and covered with a solution of 0.2 g citric acid and 10 g N-ethyl-N'-(3-dimethylaminopropyl)-carbodiimide hydrochloride in 500 ml water. After one day the arteries are washed under running water for 20 minutes and subsequently placed in a sterile physiological saline solution. They are sealed together with the liquid in a plastic bag by heat-sealing and, as described in Example 1 (c), sterilized with ethylene oxide.

EXAMPLE 16

Twenty mechanically prepared calf arteries are drawn up on glass rods, placed in a one liter measuring flask and covered with one liter tetrahydrofuran. After two and one half hours the glass rods are carefully removed from the arteries. The tetrahydrofuran is renewed. After a further five and one half hours the tetrahydrofuran is renewed a second time. Sixteen hours later, i.e. the next morning, the tetrahydrofuran is replaced with a solution of 22 g terephthalic acid dichloride in one liter tetrahydrofuran. From time to time the liquid is stirred gently with a glass rod. After 24 hours, i.e. the next morning, the solution is replaced with pure tetrahydrofuran. Six hours later the tetrahydrofuran is replaced with a mixture made of 500 ml each tetrahydrofuran and citric acid/phosphate buffer solution of pH 4.5 After two hours the mixture is replaced with a citric acid/phosphate buffer solution of pH 4.5. After being left for 16 hours the ficin treatment mentioned in Example 8 is carried out.

EXAMPLE 17

Ten calf arteries are mechanically prepared and placed vertically in a 500 ml measuring cylinder filled with tetrahydrofuran. After two and after four hours the liquid is replaced with fresh tetrahydrofuran. After a total of eight hours the liquid is replaced with a solution containing 2 g per liter trimesic acid (benzene-1,3-5-tricarboxylic acid) and 20 g per liter dicyclohexylcarbodiimide in tetrahydrofuran. The mixture is swirled a few times and allowed to stand overnight at room temperature. The next day the arteries are taken out of the solution, washed in three portions with a total of about one liter ethanol/water (1:1) (volume/volume) and subsequently placed in a citric acid/phosphate buffer solution of pH 6. They may subsequently be treated with ficin, as described in Example 7.

Instead of trimesic acid trimesitinic acid (=pyridine-2,4,6-tricarboxylic acid) or a mixture of the two acids in any ratio can also be used.

EXAMPLE 18

Eight mechanically prepared arteries are put on glass rods and placed in this state in a 500 ml measuring cylinder in the bottom of which a small magnetic stirrer is placed. Above the magnetic stirrer at a distance of about 1.5 cm from the bottom there is a perforated plate made of porcelain. The glass rods stand on this plate. 500 ml tetrahydrofuran-dimethylsulphoxide (1:1) (volume/volume) is poured in and the magnetic stirrer is set in motion. After two hours the arteries have become sufficiently stiff and the glass rods are removed. The liquid is carefully sucked off with the aid of a siphon and replaced with the same volume of tetrahydrofuran/-dimethylsulphoxide (1:1) (volume/volume). After a further six hours the liquid is replaced a second time. The next morning the liquid is replaced with a solution of 10 g furan-2,5-dicarboxylic acid dichloride in 250 ml tetrahydrofuran, again with the help of a siphon, 250 ml dimethylsulphoxide is added and this mixture is allowed to react for 24 hours. The magnetic stirrer remains constantly in motion. The liquid is then replaced with pure dimethylsulphoxide and one hour later with a citric acid/phosphate buffer solution of pH 5. After two hours later the buffer solution is renewed and allowed to stand overnight. The arteries are now ready for the ficin treatment according to Example 7 or 8.

Instead of furan-2,5-dicarboxylic acid dichloride tetrahydrofuran-2,5-dicarboxylic acid dichloride or a mixture of the two acid chlorides can be used.

EXAMPLE 19

Ten mechanically prepared calf arteries are put on glass rods and placed in a 500 ml measuring cylinder in which there is a saturated solution of D,L-camphoric acid (D,L-1,2,2-trimethylcyclopentan-1,3-cis-dicarboxylic acid) in water. After 4 hours the arteries are placed in a 500 ml measuring cylinder without the glass rods being removed and covered with a solution of 0.25 g D,L-camphoric acid and 10 g N-ethyl-N'-(3-dimethylaminopropyl)-carbodiimide-hydrochloride in 500 ml water. Four hours later the glass rods are carefully removed from the arteries. The next day the arteries are washed for half an hour under running water, placed in a sterile physiological saline solution and sealed together with the liquid in a plastic bag by heat-sealing.

Immediately afterwards they are sterilized with ethylene oxide, as described in Example 1(c).

EXAMPLE 20

Ten aorta from pigs, each about 15 cm long, are placed in a two liter measuring cylinder and covered with a tetrahydrofuran-dimethylformamide mixture (9:1) (volume/volume) until the volume comes to two liters. The liquid is renewed twice in the course of twenty-four hours. The liquid is then replaced with a mixture that contains 2 g per liter naphthalene,1,8-dicarboxylic acid and 20 g per liter dicyclohexylcarbodiimide in a tetrahydrofuran-dimethylformamide mixture (9:1) (volume/volume). The liquid is swung around several times at intervals of about two hours. The following day it is replaced with pure tetrahydrofuran, two hours later by a mixture of the same parts (volume/volume) tetrahydrofuran and a citric acid/phosphate buffer solution of pH 5 and a further two hours later with the same buffer solution of pH 5 alone. The aorta are now ready for the ficin treatment as described in Examples 7 and 8.

EXAMPLE 21

Following mechanical preparation five trachea from rabbits are placed in a 200 ml glass beaker, covered with 150 ml tetrahydrofuran and left for four hours. Thereafter, the liquid is replaced with fresh tetrahydrofuran, and again replaced a further four hours later with fresh tetrahydrofuran. The next day the liquid is poured off. Then 150 ml of a 3% solution (weight/volume) of 1,2,3,4-tetrahydronaphthalene-1,4-cis-dicarboxylic acid dichloride in tetrahydrofuran is poured over the trachea and left for one day. The liquid is then replaced with tetrahydrofuran, four hours later with a mixture of tetrahydrofuran and a citric acid/phosphate buffer solution of pH 5 (1:1) (volume/volume), and a further four hours later with a pure citric acid/phosphate buffer solution of pH 5. One day later the ficin treatment (see Example 8) is carried out.

EXAMPLE 22

Six pieces of trachea from calves, each about 12 to 15 cm long, are placed vertically in a two liter glass beaker and enough tetrahydrofuran is poured in that all the trachea pieces are covered by the liquid. After three hours the liquid is poured off and replaced with fresh tetrahydrofuran. The liquid is swirled every two hours. After a total of eight hours the liquid is renewed a second time. After a total of twenty-four hours the liquid is replaced with a solution of 2% (weight/volume) adipic acid chloride in tetrahydrofuran. The liquid is swirled about every three to four hours. The following day the liquid is poured off and fresh tetrahydrofuran is poured over the trachea pieces. About two hours and again four hours thereafter the liquid is swirled. After a further two hours it is replaced with a mixture of tetrahydrofuran and a citric acid/phosphate buffer solution of pH 4.5 (1:1) (volume/volume) and one day later with a pure aqueous citric acid/phosphate buffer solution. After standing for one day the ficin treatment is carried out as described in Example 8.

EXAMPLE 23

Following mechanical preparation a human umbilical vein is placed on an approximately 5 mm thick glass rod and together with it placed in a glass tube that is closed at one end and is approximately 2.5 cm wide and approximately 40 cm long. Enough tetrahydrofuran is added that the vein is covered. After two hours the glass rod is carefully pulled out of the vein and the tetrahydrofuran is renewed twice in the course of the next twenty-four hours. The liquid is then poured off and replaced with a 2.5% solution (weight/volume) of naphthalene-1,2-dicarboxylic acid dichloride in tetrahydrofuran. One day later the liquid is replaced with pure tetrahydrofuran, two hours later with a mixture of the same parts (volume/volume) tetrahydrofuran and a citric acid/phosphate buffer solution of pH 4.5, and a further four hours later with a pure citric acid/phosphate buffer solution of pH 4.5. The ficin treatment, as described in Example 8, is carried out the following day.

EXAMPLE 24

One hundred collaterals of calf and cattle carotid arteries, each about 2 to 4 cm long, are placed in a 200 ml glass beaker and covered with 200 ml tetrahydrofuran. The liquid is renewed twice in the course of twenty-four hours. Approximately every two hours the content of the glass beaker is carefully swung around. The following day the liquid is replaced with a tetrahydrofuran solution which contains 20 ml per liter adipic acid chloride and 38 ml per liter triethylamine. This liquid is also swirled from time to time. The following day the liquid is poured off and 200 ml tetrahydrofuran is poured over the collaterals. Two hours later the liquid is replaced with a mixture of tetrahydrofuran and a citric acid/phosphate buffer solution of pH 4.5. (1:1) (volume/volume), and a further two hours later with a pure citric acid/phosphate buffer solution of pH 4.5. One day later the collaterals are washed for a quarter of an hour under running water, placed in a sterile physiological saline solution, sealed together with the liquid in a plastic bag by heat-sealing and sterilized with ethylene oxide as described in Example 1(c).

EXAMPLE 25

Ten calf jugular veins, each about 20 to 25 cm long, are put individually on glass rods approximately 10 mm in diameter and together with it placed in glass tubes that are hermetically closed at one end and have an inner width of 2.5 cm and a length of approximately 40 cm. Each glass tube is filled with enough tetrahydrofuran that the blood vessels are completely covered by the liquid. After four hours the glass rods are removed and the liquid is renewed. After a further four hours the liquid is renewed a second time. The following day the liquid is replaced with a 2% solution (weight/volume) of succinic acid dichloride in tetrahydrofuran. From time to time, about every two to four hours, the tubes are carefully swirled. The next day the tubes are emptied, the veins are placed together in a 500 ml measuring cylinder and covered with approximately 500 ml tetrahydrofuran. Four hours later the liquid is replaced with a mixture of the same parts tetrahydrofuran and a citric acid/phosphate buffer solution of pH 4.5. A further four hours later it is replaced with a pure citric acid/phosphate buffer solution of pH 4.5. One day later the veins are subjected to the ficin treatment according to Example 8.

EXAMPLE 26

The ten calf carotid arteries, each approximately 20 cm long and having an inner width of about 6 to 7 mm, are carefully put on to 8 mm thick glass rods that are rounded off at both ends, are placed in a 500 ml measuring cylinder and covered with enough tetrahydrofuran that all the carotid arteries are covered by the liquid. After two hours the glass rods are carefully removed. The carotid arteries are now quite stiff; they keep the inner diameter of 8 mm and afterwards prove to be even more elastic. They are placed in fresh tetrahydrofuran which is renewed after four hours. The following day the liquid is replaced with a 2% (weight/volume) solution of glutaric acid dichloride in tetrahydrofuran and left standing for one day. The liquid is then replaced with pure tetrahydrofuran and four hours later with a mixture of equal parts (volume/volume) tetrahydrofuran and a citric acid/phosphate buffer solution of pH 4.5. A further four hours later the liquid is replaced with a citric acid/phosphate buffer solution of pH 4.5. The following day the carotid arteries may be subjected to the ficin treatment described in Example 8.

EXAMPLE 27

Ten round pieces 3 cm in diameter are cut from a calf pericardium and placed in water for half an hour. Each piece is individually placed on a spur-shaped former which itself is about 8 mm in diameter and which projects about 2 cm from a plate. The pericardium pieces are pressed on all sides from the centre out on to the former with a smooth modelling stick and gradually modelled on to it. They thereby obtain the shape of a sack approximately 8 mm in diameter and 12 mm high. If the former together with the pericardium pieces put over it are placed under a 100 watt spot lamp for 20 minutes, the pericardium pieces dry on it and can be stripped off the block without losing their shape. They are now all placed together in a glass beaker in which there is 150 ml tetrahydrofuran and are carefully pressed under the surface of the liquid. The tetrahydrofuran is renewed after three and after six hours. The following day the liquid is replaced with a 3.2% solution (weight/volume) of dodecanedioic acid dichloride in tetrahydrofuran and the pericardium sacks are left in it for twenty-four hours. The liquid is then replaced with pure tetrahydrofuran, four hours later with a mixture of tetrahydrofuran and a citric acid/phosphate buffer solution of pH 4.5 (1:1) (volume/volume) and a further four hours later with a pure citric acid/phosphate buffer solution of pH 4.5. The next day the pericardium sacks are placed in a sterile physiological saline solution, sealed together with the liquid in plastic bags and sterilized immediately afterwards with ethylene oxide. They may be used as a tympanic membrane substitute.

EXAMPLE 28

Five calf arteries, each about 22 cm long and approximately 5 mm wide, are each carefully drawn up on a 3 mm thick, U-shaped glass rod, in which the two legs of the U-shaped glass rod are about 3.5 cm apart. The arteries together with the glass rods are placed in a round glass dish approximately 25 cm in diameter and covered with enough tetrahydrofuran that the surface of the liquid is about 2 cm above the arteries. The glass dish is covered with aluminum foil so that the tetrahydrofuran does not evaporate. After two hours the glass rods are carefully removed and the tetrahydrofuran is renewed. The arteries now maintain the U-shape. After a further five hours the tetrahydrofuran is renewed a second time. After a total of twenty-four hours the liquid is replaced with a 2.9% (weight/volume) solution of pyridine-2,3,6-tricarboxylic acid trichloride in tetrahydrofuran and left to stand for twenty-four hours, covered as before with aluminum foil. The solution is then poured off and pure tetrahydrofuran is poured over the arteries. Two hours later the liquid is replaced with a mixture of equal parts (volume/volume) tetrahydrofuran and a citric acid/phosphate buffer solution of pH 4.5, and a further two hours later with a pure citric acid/phosphate buffer solution of pH 4.5. The following day the arteries are subjected to the ficin treatment as described in Example 8. The U-shaped arteries are placed in the measuring cylinder in such a way that the curvature projects downwards and the legs of the U project upwards. Following treatment with the ficin and sodium chlorite the arteries are placed in a large, approximately 8 cm deep glass dish and washed with running deionised water for a quarter of an hour. Afterwards the water is poured off and the arteries are placed in a 0.1% (weight/volume) aqueous solution of glutaraldehyde. Three days later the liquid is poured off. The arteries are then washed for half an hour under running water. They are then placed in 0.9% sodium chlorite solution, filled together with the solution in plastic bags which are sealed and then sterilized with ethylene oxide as described in Example 1, section (c).

We claim:

1. A process for the preparation of new organ transplants from organs and parts of organs of fish, birds and mammals, which comprises subjecting said organs and parts of organs to crosslinking between the peptide chains of the intercellular matrix and a crosslinking agent selected from the group of dicarboxylic, tricarboxylic and polycarboxylic acids of the aliphatic, cycloaliphatic, aromatic and heterocyclic series, said crosslinking being effected by formation of amide bonds and ester bonds between the amino groups and the alcoholic hydroxyl groups, respectively, of said peptide chains, and the carboxylic groups of said crosslinking agent.

2. A process according to claim 1, wherein said di-, tri-, or poly-carboxylic acids contain neither aldehyde nor keto groups nor amino groups.

3. A process according to claim 1, wherein said di, tri- or poly-carboxylic acids contain no functional groups other than carboxylic groups.

4. A process according to claim 1, wherein said di-, tri- or poly-carboxylic acids contain no functional groups other than carboxylic and hydroxyl groups.

5. A process according to claim 2, wherein said di-, tri- or poly-carboxylic acids are selected from the group comprising aliphatic carboxylic acids having 3 to 12 carbon atoms, cyclopentane- and cyclohexane-dicarboxylic acids, phthalic acid, isophthalic acid, terephthalic acid, trimesic and trimellitic acid and furan- and tetrahydrofuran-2, 5-dicarboxylic acid, oxidized starch and carboxymethylcellulose.

6. A process according to one of claims 1, 2 or 5, wherein said resulting intercellular matrix crosslinked by amide bonds is additionally treated with formaldehyde or a dialdehyde.

7. A process according to claim 6, wherein said dialdehyde is dialdehyde starch or glutaraldehyde.

8. A process according to one of claims 1, 2 or 5, wherein material which is present in the resulting intercellular matrix crosslinked by amide bonds and which potentially can act as an antigen is additionally degraded by hydrolysis with ficin, papaine or any other protease having the same substrate specifity as ficin or papaine.

9. A process according to claim 8, wherein the hydrolysis is carried out with ficin.

10. A process according to claim 8, wherein the resulting matrix, which is crosslinked by amide bonds and is antigen-free, is additionally treated with formaldehyde or a dialdehyde.

11. A process according to claim 8, wherein the resulting matrix, which is crosslinked by amide bonds and is antigen-free, is additionally subjected to further crosslinking by the formation of amide bonds between free amino groups and the carboxylic groups of dicarboxylic acids, tricarboxylic acids or polycarboxylic acids of the aliphatic, cycloaliphatic, aromatic or heterocyclic series.

12. Organ transplants obtained by the process according to one of claims 1 to 11.

* * * * *